(12) United States Patent
Kroll et al.

(10) Patent No.: US 10,039,919 B2
(45) Date of Patent: Aug. 7, 2018

(54) METHODS AND APPARATUS FOR DETECTING AND LOCALIZING PARTIAL CONDUCTOR FAILURES OF IMPLANTABLE DEVICE LEADS

(71) Applicant: Lambda Nu Technology LLC, Orono, MN (US)

(72) Inventors: Mark W. Kroll, Crystal Bay, MN (US); Charles D. Swerdlow, Los Angeles, CA (US)

(73) Assignee: Lambda Nu Technology LLC, Orono, MN (US)

( * ) Notice: Subject to any disclaimer, the term of this patent is extended or adjusted under 35 U.S.C. 154(b) by 314 days.

(21) Appl. No.: 14/224,281

(22) Filed: Mar. 25, 2014

(65) Prior Publication Data

US 2014/0324123 A1  Oct. 30, 2014

Related U.S. Application Data

(60) Provisional application No. 61/817,667, filed on Apr. 30, 2013.

(51) Int. Cl.
*A61N 1/08* (2006.01)
*A61N 1/05* (2006.01)
*A61B 5/0424* (2006.01)

(52) U.S. Cl.
CPC .............. *A61N 1/08* (2013.01); *A61N 1/0563* (2013.01); *A61B 5/0424* (2013.01); *A61B 2560/0276* (2013.01); *A61N 2001/083* (2013.01)

(58) Field of Classification Search
CPC ..................................................... A61N 1/08
(Continued)

(56) References Cited

U.S. PATENT DOCUMENTS 3,599,055 A  8/1971  Bloom
4,766,549 A  8/1988  Schweitzer, III et al.
(Continued)

FOREIGN PATENT DOCUMENTS

EP  0288630 B1  11/1988
EP  2032027 B1  10/2011

OTHER PUBLICATIONS

"Agilent Impedance Measurement Handbook A Guide to Measurement Technology and Techniques 4th Edition," Agilent Technologies, Inc., Jun. 17, 2009, 140 pages.
(Continued)

*Primary Examiner* — Nadia A Mahmood
(74) *Attorney, Agent, or Firm* — Patterson Thuente Pedersen, P.A.

(57) ABSTRACT

Method and apparatus for diagnosis of conductor anomalies, such as partial conductor failures, in an implantable lead for an implantable medical device are disclosed. In various embodiments, small changes in the lead impedance are identified by the use of a small circuit element that is incorporated as part of the distal end of the implantable lead. In various embodiments, the small circuit element is electrically connected to a lead conductor and/or electrode of the implantable lead. Methods of diagnosing conductor anomalies in accordance with these embodiments generate measured values that depend only on the impedance of the conductors and electrodes of the lead, and not on the behavior of the conductor-tissue interface and other body tissues.

13 Claims, 8 Drawing Sheets

(58) Field of Classification Search
USPC .......................................... 607/59, 3, 5, 27
See application file for complete search history.

(56) References Cited

U.S. PATENT DOCUMENTS

| | | | |
|---|---|---|---|
| 5,003,975 A | 4/1991 | Hafelfinger et al. | |
| 5,231,987 A | 8/1993 | Robson | |
| 5,243,980 A | 9/1993 | Mehra | |
| 5,361,776 A | 11/1994 | Samuelson et al. | |
| 5,405,363 A | 4/1995 | Kroll et al. | |
| 5,453,698 A | 9/1995 | Williams et al. | |
| 5,557,210 A | 9/1996 | Cappa et al. | |
| 5,741,311 A | 4/1998 | McVenes et al. | |
| 5,755,742 A | 5/1998 | Schuelke et al. | |
| 5,897,577 A | 4/1999 | Cinbis et al. | |
| 5,944,746 A | 8/1999 | Kroll | |
| 6,104,954 A | 8/2000 | Blunsden | |
| 6,317,633 B1 | 11/2001 | Jorgenson et al. | |
| 6,415,179 B1 | 7/2002 | Pendekanti et al. | |
| 6,445,951 B1 | 9/2002 | Mouchawar | |
| 6,490,486 B1 | 12/2002 | Bradley | |
| 6,580,948 B2 | 6/2003 | Haupert et al. | |
| 6,928,325 B2 | 8/2005 | Zhu et al. | |
| 7,047,083 B2 | 5/2006 | Gunderson et al. | |
| 7,081,130 B2 | 7/2006 | Jang | |
| 7,120,563 B2 | 10/2006 | Bechhoefer et al. | |
| 7,289,851 B2 | 10/2007 | Gunderson et al. | |
| 7,369,893 B2 | 5/2008 | Gunderson | |
| 7,454,249 B1 | 11/2008 | Bornzin et al. | |
| 7,623,919 B2 | 11/2009 | Goetz et al. | |
| 7,747,320 B1 | 6/2010 | Kroll et al. | |
| 7,764,998 B1 | 7/2010 | Raddatz | |
| 8,200,330 B2 | 6/2012 | Kroll et al. | |
| 8,352,033 B2 | 1/2013 | Kroll | |
| 8,457,742 B2 | 6/2013 | Jacobson | |
| 8,463,382 B2 | 6/2013 | Jorgenson et al. | |
| 8,463,384 B2 | 6/2013 | Germanson et al. | |
| 8,467,872 B2 | 6/2013 | Hareland | |
| 8,498,706 B2 | 7/2013 | Pei et al. | |
| 8,577,457 B2 | 11/2013 | Miller et al. | |
| 8,644,932 B2 | 2/2014 | Seifert et al. | |
| 8,682,436 B2 | 3/2014 | Ghosh et al. | |
| 8,700,156 B2 | 4/2014 | Kroll | |
| 8,812,103 B2 | 8/2014 | Kroll et al. | |
| 8,825,158 B2 | 9/2014 | Swerdlow | |
| 9,272,150 B2 | 3/2016 | Kroll et al. | |
| 9,427,577 B2 | 8/2016 | Kroll et al. | |
| 9,486,624 B2 | 11/2016 | Swerdlow | |
| 9,675,799 B2 | 6/2017 | Kroll et al. | |
| 9,814,876 B2 | 11/2017 | Swerdlow | |
| 9,821,156 B2 | 11/2017 | Kroll et al. | |
| 9,827,416 B2 | 11/2017 | Swerdlow | |
| 2003/0004552 A1* | 1/2003 | Plombon | A61N 1/3956 607/27 |
| 2003/0036772 A1 | 2/2003 | Saphon et al. | |
| 2004/0010303 A1 | 1/2004 | Bolea et al. | |
| 2004/0068301 A1 | 4/2004 | Waltman et al. | |
| 2004/0158290 A1 | 8/2004 | Girouard et al. | |
| 2004/0230385 A1 | 11/2004 | Bechhoefer et al. | |
| 2005/0137636 A1 | 6/2005 | Gunderson et al. | |
| 2005/0187586 A1 | 8/2005 | David et al. | |
| 2005/0256547 A1 | 11/2005 | Stahmann et al. | |
| 2006/0025828 A1 | 2/2006 | Armstrong et al. | |
| 2006/0116747 A1 | 6/2006 | Eick et al. | |
| 2006/0135886 A1 | 6/2006 | Lippert et al. | |
| 2006/0241513 A1 | 10/2006 | Hatlestad | |
| 2006/0265038 A1 | 11/2006 | Hagen et al. | |
| 2007/0208387 A1 | 9/2007 | Mower | |
| 2008/0208271 A1 | 8/2008 | Sih et al. | |
| 2008/0309351 A1 | 12/2008 | Stewart et al. | |
| 2009/0099615 A1 | 4/2009 | Kroll | |
| 2009/0270938 A1 | 10/2009 | Pei et al. | |
| 2009/0292331 A1 | 11/2009 | Gunderson et al. | |
| 2009/0299431 A1 | 12/2009 | Schecter | |
| 2009/0299432 A1 | 12/2009 | Stadler et al. | |
| 2009/0306735 A1 | 12/2009 | Lagercrantz et al. | |
| 2010/0179446 A1 | 7/2010 | Bojovic et al. | |
| 2010/0179538 A1 | 7/2010 | Podhajsky | |
| 2010/0204758 A1 | 8/2010 | Boon et al. | |
| 2010/0228307 A1 | 9/2010 | Kroll et al. | |
| 2010/0324629 A1 | 12/2010 | Jorgenson et al. | |
| 2011/0054554 A1 | 3/2011 | Swerdlow | |
| 2011/0054556 A1 | 3/2011 | Swerdlow | |
| 2011/0054558 A1 | 3/2011 | Gunderson et al. | |
| 2011/0160808 A1 | 6/2011 | Lyden et al. | |
| 2011/0160829 A1 | 6/2011 | Foster et al. | |
| 2011/0230741 A1 | 9/2011 | Liang et al. | |
| 2012/0035491 A1 | 2/2012 | Mahajan et al. | |
| 2012/0191153 A1 | 7/2012 | Swerdlow et al. | |
| 2012/0197331 A1* | 8/2012 | Germanson | A61N 1/3706 607/11 |
| 2012/0197365 A1 | 8/2012 | Germanson et al. | |
| 2013/0013038 A1 | 1/2013 | Miller | |
| 2013/0030496 A1 | 1/2013 | Karamanoglu et al. | |
| 2013/0123871 A1 | 5/2013 | Kroll | |
| 2013/0165986 A1 | 6/2013 | Ghosh et al. | |
| 2013/0304139 A1 | 11/2013 | Musley et al. | |
| 2013/0304160 A1 | 11/2013 | Gunderson et al. | |
| 2013/0325079 A1 | 12/2013 | Kroll et al. | |
| 2013/0325080 A1 | 12/2013 | Kroll et al. | |
| 2014/0018873 A1 | 1/2014 | Gunderson | |
| 2014/0155947 A1 | 6/2014 | Kroll et al. | |
| 2014/0371831 A1 | 12/2014 | Swerdlow | |
| 2015/0005862 A1 | 1/2015 | Kroll et al. | |
| 2015/0088213 A1 | 3/2015 | Swerdlow | |
| 2015/0151118 A1 | 6/2015 | Kroll et al. | |
| 2015/0273225 A1 | 10/2015 | Swerdlow et al. | |
| 2016/0250462 A1 | 9/2016 | Kroll et al. | |
| 2016/0271390 A1 | 9/2016 | Kroll et al. | |
| 2016/0375239 A1 | 12/2016 | Swerdlow | |
| 2017/0120045 A1 | 5/2017 | Swerdlow | |

OTHER PUBLICATIONS

Armour, Andrew J., et al., "Gross and Microscopic Anatomy of the Human Intrinsic Cardiac Nervous System," Anatomical Record, 1997, pp. 289-298.

Balkhy, Husam H., et al., "Autonomic Ganglionated Plexi: Characterization and Effect of Epicardial Microwave Ablation in a Canine Model of Vagally Induced Actue Atrial Fibrillation," Meeting for the International Society for Minimally Invasive Cardiothoracic Surgery (Abstract), 2006.

Brewer et al., "Low Voltage Shocks Have a Significantly Higher Tilt of the Internal Electric Field Than Do High Voltage Shocks," Angeion Corporation, Jan. 1995, Part II, PACE, vol. 18, pp. 214-220.

Chevalier, P., "Quantitative Study of Nerves of the Human Left Atrium," Heart Rhythm, 2005, pp. 518-522.

Dilling-Boer, Dagmara et al., "Ablation of Focally Induced Atrial Fibrillation: Selective or Extensive?," J. Cardio. Electryphys., 2004, pp. 200-205.

Haissaguerre, Michel et al., "Pulmonary Veins in the Substrate for Atrial Fibrillation: The "venous wave" Hypothesis," 2004, pp. 2290-2292.

Haissaguerre, Michel et al., "Spontaneous Initiation of Atrial Fibrillation by Ecoptic Beats Originating in the Pulmonary Veins," NEJM, 2006, pp. 659-666.

Kilgore, K.L., et al., "Nerve Conduction Block Utilising High-Frequency Alternating Current," Med. Biol. Eng. Comput., 2004, pp. 394-406.

Kumagai, K., et al., "Electrophysiologic Properties of Pulmonary Veins Assessed Using a Multielectrode Basket Catheter," 2004, pp. 2281-2289.

Levy, S., "Characterization of Different Subsets of Atrial Fibrillation in General Practice in France: The ALFA Study," The College of French Cardiologists, Circulation, 1999, pp. 3028-3035.

Lo et al., "Noise-Doman Reflectometry for Locating Wiring Faults," IEEE Transactions on Electromagnetic Compatibility, vol. 47, No. 1, Feb. 2005.

(56) References Cited

OTHER PUBLICATIONS

Nathan, H., et al., "The Junction Between the Left Atrium and the Pulmonary Veins: An Anatomic Study of Human Hearts," Circulation, 1966, pp. 412-422.
Oh., S., "Vagal Denervation and Atrial Fibrillation Inducibility: Epicardial Fat Pad Ablation Does Not Have Long-Term Effects," Heart Rhythm, 2006, pp. 701-708.
Oral, Hakan et al., "Pulmonary Vein Isolation for Paroxysmal and Persistent Atrial Fibrillation," Circulation, 2002, pp. 1077-1081.
Pappone, Carlo, "Pulmonary Vein Denervation Enhances Long-Term Benefit After Circumferential Ablation for Paroxysmal Atrial Fibrillation," Circulation, 2004, pp. 327-334.
Patterson, E. et al., "Triggered Firing in Pulmonary Veins Initiated by In Vitro autonomic nerve stimulation," Heart Rhythm, 2005, pp. 624-631.
Patterson, Eugene et al., "Sodium-Calcium Exchange Initiated by the Ca2+ Transient: An Arrhythimia Trigger Within Pulmonary Veins," J. Am. Coll. Cardiol, 2006, pp. 1196-1206.
Po Sunny S., et al., "Rapid and Stable Re-entry within the Pulmonary Vein as a Mechanism Initiating Paroxysmal Atrial Fibrillation," J.Am Coll. Cariol., 2005, pp. 1871-1877.
Po, Sunny S. et al., "Experimental Model for Paroxysmal Atrial Fibrillation Arising at the Pulmonary Vein-Atrial Junctions," Heart Rhythm, 2006, pp. 201-208.
Randall, David C., et al., "Ablation of Posterior Atrial Ganglionated Plexus Potentiates Sympathetic Tachycardia to Behavioral Stress," Comp. Physiol., 1998, pp. 779-787.
Schauerte, P., et al., "Ventricular Rate Control During Atrial Fibrillation by Cardiac Parasympathetic Nerve Stimulation: A Transvenous Approach," J. Am. Coll. Cardiol., 1999, pp. 2043-2050.
Schauerte, Patrick et al., "Catheter Ablation of Cardiac Autonomic Nerves for Prevention of Vagal Atrial Fibrillation," Circulation, 2000, pp. 2774-2780.
Schauerte, Patrick, "Focal Atrial Fibrillation: Experimental Evidence for a Pathophysiologic Role of the Autonomic Nervous System," Cardiovasc. Electrophysiol., 2001, pp. 592-599.
Scherlag, Benjamin J., et al., "Autonomically Induced Conversion of Pulmonary Vein Focal Firing Into Atrial Fibrillation," J. Am Coll. Cardiol., 2005, pp. 1878-1886.
Scherlag, Benjamin, "Electrical Stimulation to Identify Neural Elements on the Heart: Their Role in Atrial Fibrillation," J. Interv. Card, Electrophysiol, 2005, pp. 37-42.
Tai, C., "Stimulation Analysis of Conduction Block in Unmyelinated Axons Induced by High-Frequency Biphasic Electrical Currents," IEEE T-BME, 2005, p. 1323.
Tchou et al., "The AngeMed Sentinel Implantable Antitachycardia Pacer Cardioverter-Defibrillator," Implantable Cardioverter-Defibrillators: A Comprehensive Textbook, Copyright 1994, pp. 755-761.
Tomasic, "Acute and Chronic High-Frequency Properties of Cardiac Pacing and Defibrillation Leads," Med Biol Eng Comput 50:827-837, 2012.
Ellenbogen, "Performance of ICD Lead Integrity Alert to Assist in the Clinical Diagnosis of ICD Lead Failures: Analysis of Different ICD Leads," Circulation Arrhythmia and Electrophysiology, Oct. 7, 2013.
Swerdlow, "Downloadable Algorithm to Reduce Inappropriate Shocks Caused by Fractures of Implantable Cardioverter-Defibrillator Leads," Circulation Journal of the American Heart Association, Nov. 3, 2008, 9 pages.
Swerdlow, "Downloadable Software Algorithm Reduces Inappropriate Shocks Caused by Implantable Cardioverter-Defibrillator Lead Fractures—A Prospective Study," Circulation Journal of the American Heart Association, Sep. 27, 2010, 8 pages.
Application and File history for U.S. Appl. No. 12/868,056, filed Aug. 25, 2010, now U.S. Pat. No. 8,825,158. Inventor Swerdlow.
Application and File history for U.S. Appl. No. 13/735,599, filed Jan. 7, 2013, now U.S. Pat. No. 8,700,156. Inventor Kroll.
Application and File history for U.S. Appl. No. 13/842,838, filed Mar. 15, 2013. Inventor Kroll.
Application and File history for U.S. Appl. No. 12/252,310, filed Oct. 15, 2008, now U.S. Pat. No. 8,352,033. Inventor: Kroll.
Application and File history for U.S. Appl. No. 13/843,145, filed Mar. 15, 2013, now U.S. Pat. No. 8,812,103. Inventors: Kroll et al.
Application and File history for U.S. Appl. No. 13/833,477, filed Mar. 15, 2013. Inventors: Kroll et al.
Application and File history for U.S. Appl. No. 14/224,876, filed Mar. 25, 2014. Inventors: Kroll et al.
Application and File history for U.S. Appl. No. 14/203,688, filed Mar. 11, 2014. Inventors: Kroll et al.
Application and File history for U.S. Appl. No. 14/224,335, filed Mar. 25, 2014. Inventors: Kroll et al.
Application and File history for U.S. Appl. No. 14/453,679, filed Aug. 7, 2014. Inventors: Kroll et al.
Application and File history for U.S. Appl. No. 14/472,027, filed Aug. 28, 2014. Inventors: Kroll et al.
PCT Application No. PCT/US2013/043386, filed May 30, 2013, Search Report and Written Opinion dated Sep. 27, 2013, 10 pages.
PCT Application No. PCT/US2013/043389, filed May 30, 2013, Search Report and Written Opinion dated Sep. 5, 2013, 9 pages.
PCT Application No. PCT/US2013/072957, Filed Dec. 4, 2013, Search Report and Written Opinion dated Mar. 6, 2014.
PCT Application No. PCT/US2015/022435, Filed Mar. 25, 2015, Search Report and Written Opinion dated Jun. 29, 2015.
EP Application No. 13796833.5, Extended EP Search Report dated Feb. 11, 2016, 9 pages.
European Extended Search Report; EP Application No. 13859688.7, dated May 27, 2016, 11 pages.

* cited by examiner

METHODS AND APPARATUS FOR DETECTING AND LOCALIZING PARTIAL CONDUCTOR FAILURES OF IMPLANTABLE DEVICE LEADS

RELATED APPLICATION

The present application claims the benefit of U.S. Provisional Application No. 61/817,667 filed Apr. 30, 2013, which is incorporated herein in its entirety by reference.

FIELD OF THE INVENTION

The present invention relates, generally, to scientific and medical systems, apparatus, and methods. More particularly, the invention relates to method and apparatus for diagnosis of conductor anomalies, such as partial conductor failures, in an implantable lead for an implantable medical device by identifying small changes in the lead impedance by the use of a small circuit element that is connected near the distal end of the lead.

BACKGROUND

The long-term reliability and safety of implantable cardiac leads is a significant issue. Anomalies of conductors in implantable medical devices constitute a major cause of morbidity. Representative examples of such medical devices include, but are not limited to, pacemakers, vagal nerve stimulators, pain stimulators, neurostimulators, and implantable cardioverter defibrillators (ICDs). "Multilumen" ICD defibrillation leads include one or more high-voltage conductors and one or more pace-sense conductors. The leads can be implanted as subcutaneously or intravascularly. The lead body consists of a flexible, insulating cylinder having three to six longitudinal lumens configured in parallel. Conductors are disposed in the lumens providing an electrical pathway between the proximal terminals to small pace-sense electrodes and larger shock coil electrodes.

Early diagnosis of ICD lead conductor anomalies is important to reduce morbidity and/or mortality. Anomalies may occur in either the pace-sense or shock components. The most common presentation of pace-sense failures is oversensing of rapid, nonphysiological signals. Prior to the implementation of diagnostics that incorporated oversensing, pace-sense fractures presented most commonly as inappropriate shocks, despite daily, automated measurements of pacing impedance. Functional failure of a pace-sense conductor or oversensing also results in inhibition of bradycardia pacing, cardiac resynchronization, or antitachycardia pacing. Lead insulation failure or fractures may also present with loss of capture. High-voltage conductor failures present with potentially fatal failed defibrillation or cardioversion. Thus, early diagnosis of ICD lead conductor anomalies is a critically important step in reducing morbidity and/or mortality from the failure of pacing, inappropriate ICD shocks, and/or ineffective treatment of ventricular tachycardia or fibrillation (ventricular fibrillation). The early diagnosis of conductor anomalies for implantable cardiac leads is a critically important step in reducing these issues and making ICDs safer.

Thus, one major goal is high sensitivity of diagnosis: identification of lead conductor failures at the subclinical stage, before they present as a clinical problem. A second major goal is high specificity: a false positive provisional clinical diagnosis of lead insulation failure may trigger patient anxiety and lead to potentially avoidable diagnostic testing. A false positive clinical diagnosis of insulation failure results in unnecessary lead replacement, with corresponding expense and surgical risk.

Currently, the primary method, of which various methods are well-known in the art, for monitoring pacemaker and ICD lead integrity is periodic measurement of electrical resistance, commonly referred to as "impedance monitoring." The current art impedance monitoring methods use single pulses and provide a value of impedance close to the direct-current resistance.

For pace-sense conductors, the circuit being measured comprises the connection between the implantable pulse generator header and the lead, the conductors to the tip and ring electrodes, and the electrode-myocardial interface. Most of the resistance is at the electrode-tissue interface of the high-resistance tip electrode, and variations of up to 10% in this value are common. Each individual pace-sense conductor (for example, the conductor to the tip electrode or the ring electrode) contributes less than 10% to the measured resistance. Thus, even if the pace-sense resistance in a single conductor doubled or tripled, the overall measured resistance remains within the expected range.

In fact, with presently-used methods, abnormal increases in impedance occur before diagnostic oversensing—and usually shocks—in only 28% of confirmed Fidelis fractures. For example, the normal resistance of the ring connecting cable (in a Riata® lead) is only 13Ω. This connection has two cables in parallel, with each cable having a normal resistance of 26Ω. In the case of one of the two cables being completely severed, the impedance thus only increase to 26Ω while the impedance seen by the conventional lead impedance "monitoring"—which includes the impedance of the electrode-electrolyte impedance and the return through another electrode—is around 500Ω to 2 kΩ and is thus undetectable. The normally sensed impedance will typically vary by hundreds of ohms during the course of the implant and thus a change of 13Ω is nominal and is easily missed.

Therefore, measurements indicate that resistance does not exceed the expected range until the conductor has lost most of its structural integrity and resistance remains within the expected range even when only a fraction of the conductor is intact.

Further, resistance measurements have limited specificity. A single, out-of-range value may be an artifact, and marked, persistent increases can occur at the electrode-myocardial interface in normally functioning leads, thus resulting in over diagnosis of lead failures.

Hafelinger et al. (U.S. Pat. No. 5,003,975) and Cinbis et al. (U.S. Pat. No. 5,897,577) summarize some of these methods, which include measurements made directly using either a single pacing pulse or a single independent pulse used only for measuring resistance. McVenes et al. (U.S. Pat. No. 5,741,311) describes use of a longer burst of alternating current at a single frequency. The purpose of these longer (about 100 ms) pulses is to drive the system to a steady-state condition that is not achieved by single, short (less than 1 ms) pacing pulse. Schuelke et al. (U.S. Pat. No. 5,755,742) describes a method for measuring resistance of defibrillation electrodes by applying a test voltage applied to a different excitation current pathway. Kroll et al. (U.S. Pat. No. 5,944,746) describes an automated method for periodic measurement of the resistance of the high-voltage (defibrillating) coil in ICD electrodes. Gunderson et al. (U.S. Pat. No. 7,047,083) describes a method and system for automated periodic measurements of resistance in conductors attached to an ICD or pacemaker. However, these types of "impedance monitoring," which return values close to direct current resistance, identify lead anomalies before inappropriate shocks in only about a third of ICD patients who have conductor fractures.

A newer method for monitoring ICD lead integrity is based on the response of ICD pulse generators to electrical "noise" signals associated with lead conductor fractures. These nonphysiological signals have specific characteristics that differentiate them from true cardiac signals such as high variability and, at times, nonphysiologically-rapid rates. If these signals are of sufficient amplitude and exceed the ICD's dynamically-changing sensing threshold, the ICD oversenses them. Repetitive oversensing of nonphysiologically-short intervals may indicate lead conductor fracture even if lead resistance is normal. Gunderson et al. (U.S. Pat. No. 7,289,851) described a Lead-Integrity Alert that incorporates both ICD-based measures of oversensing based on the nonphysiologically-rapid rate of sensed signals and periodic measurements of resistance. This method, combined with automatic ICD reprogramming, improves warning time before inappropriate shocks caused by lead-related oversensing. Nevertheless, approximately 25% of patients receive less than 3 days of warning, and some receive almost no warning.

Additionally, the Gunderson Lead Integrity Alert method detects only some lead-noise signals. It cannot detect a lead anomaly unless it generates signals that are both fast enough and of sufficient amplitude to be classified as nonphysiological oversensing. Thus, it will not detect a lead anomaly if it does not generate "noise signals" or if it generates only low-amplitude noise signals, or signals that do not occur at a fast enough rate.

Gunderson et al. (U.S. Pat. No. 7,369,893) describes a method for withholding delivery of ICD shocks if ventricular fibrillation is detected from analysis of the pace-sense lead, but is not confirmed by analysis of the high-voltage lead. Although not yet evaluated in patients, this method is expected to further reduce unnecessary shocks. However, it requires sufficient oversensing to result in inappropriate detection of ventricular fibrillation clinically. Thus, it does not provide early diagnosis of conductor anomalies. Withholding shocks for ventricular fibrillation detected on the near-field electrogram has an inherent risk of withholding life-saving therapy, however small, and is, thus, not the preferred approach to diagnosis conductor fracture. Like the Lead-Integrity Alert method, it is not applicable to intraoperative diagnosis or to pacemakers and neurostimulators.

Comparable limitations apply to measuring impedance of the high-voltage lead components. The circuit measured comprises the connection between the implantable pulse generator header and lead, high-voltage conductor cables, shock electrodes, blood in the right atrium and ventricle, and—providing the CAN or ICD housing is included—heart, lung, and chest wall. High-voltage cables and shock electrodes have low impedance (~1Ω), and the overall circuit typically has resistance in the range of 30Ω to 80Ω. Thus, impedance measurements are correspondingly insensitive to significant changes in cable or coil impedance.

The difficulty in detecting a partial failure with present electrical testing may also be appreciated from the following example. Consider a fracture in the conductor leading to the RV coil (RV conductor). The typical SVC coil has an impedance on the order of 60Ω through to another electrode or the CAN, while the cable connection impedance is only about 1.5Ω (from the combination of two cables in parallel, each having impedance of 3Ω). Thus, the complete fracture of one of the two cables would result in an impedance increase of only 1.5Ω, which is far lower than the typical (5Ω to 10Ω) serial impedance changes seen chronically.

In addition to limited sensitivity, present methods for diagnosing lead conductor anomalies have limited specificity resulting in false positive diagnostics. Evaluation of false positive diagnostics adds cost and work to medical care and may contribute to patient anxiety. If a false-positive diagnostic is not diagnosed correctly, patients may be subject to unnecessary surgical lead replacement with its corresponding risks.

Any clinical method for detecting conductor anomalies in implanted leads must make measurements while the conductor and lead are in the body. Typically, the measuring circuit includes the conductor-tissue interface in the body. Thus, the measured values will depend both on the behavior of the conductor being evaluated and the conductor-tissue interface.

Existing technology for diagnosis of conductor anomalies in an implantable medical device is believed to have significant limitations and shortcomings. What is desired are method and apparatus that could analyze and identify implantable cardiac lead conductor anomalies at the subclinical stage, before they present as a clinical problem, and do so with a high sensitivity and specificity that minimizes false positives for implantable cardiac lead conductor anomalies.

SUMMARY OF THE INVENTION

The disclosed method and apparatus relates to the diagnosis of conductor anomalies, such as partial conductor failures, in an implantable lead for use with an implantable medical device, such as an implantable cardioverter defibrillator (ICD), a pacemaker, or a neurostimulator. The disclosed method and apparatus removes the conductor-tissue interface in the body and body tissues from the measuring circuit by the incorporation of a small circuit element as part of the distal end of the implantable lead. In various embodiments, the small circuit element is electrically connected to a lead conductor and/or electrode of the implantable lead. In various embodiments, methods of diagnosing conductor anomalies will generate measured values that depend only on the impedance of the conductors and electrodes of the lead, and not on the behavior of the conductor-tissue interface and other body tissues.

BRIEF DESCRIPTION OF THE DRAWINGS

The invention may be more completely understood in consideration of the following detailed description of various embodiments of the invention in connection with the accompanying drawings, in which.

Figure 1:
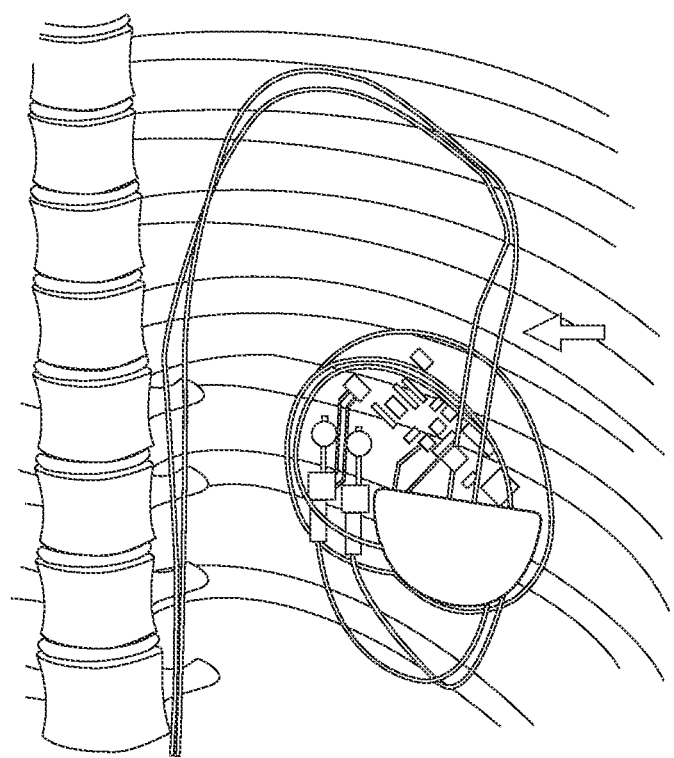
FIG. 1 shows a radiograph or x-ray of an implantable cardioverter defibrillator (ICD) implanted in a human body where the lead has a small area of stress from a tight suture.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The embodiments herein are directed to the diagnosis of lead or conductor anomalies, such as insulation failures, in an implantable medical device, such as pacemakers, vagal nerve stimulators, pain stimulators, neurostimulators, and implantable cardioverter defibrillators (ICDs). However, for clarity, discussion of lead or conductor anomalies will be made in reference to ICDs. However, those with skill in the art are cognizant of the fact that the methods and apparatus as disclosed herein are suitable for use with any one of the various implantable medical devices.

FIG. 1 depicts a radiograph or x-ray of an implantable cardioverter defibrillator (ICD) implanted in a human body where the lead has a small area of stress from a tight suture.

Figure 2A:
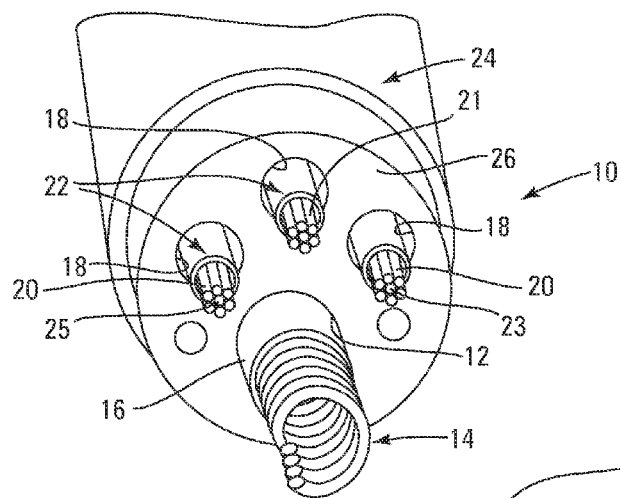
FIG. 2A is a cross-sectional view of the Medtronic Quattro Secure® Lead, a multi-lumen ICD implantable cardiac lead.
Figure 2B:
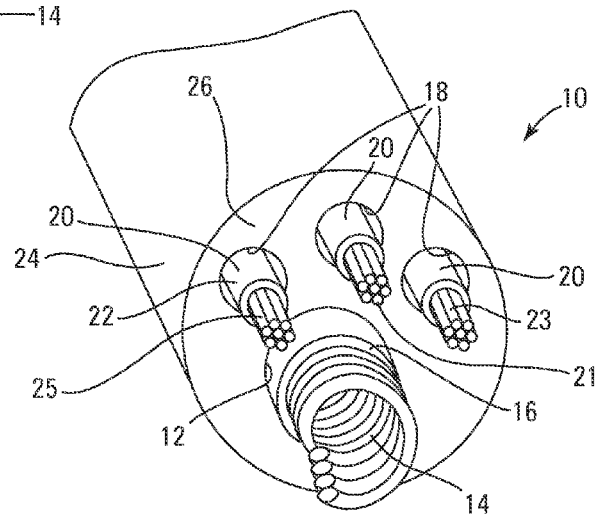
FIG. 2B is a cross-sectional view of the Medtronic Sprint Fidelis® Lead, a multi-lumen ICD implantable cardiac lead.
Figure 3:
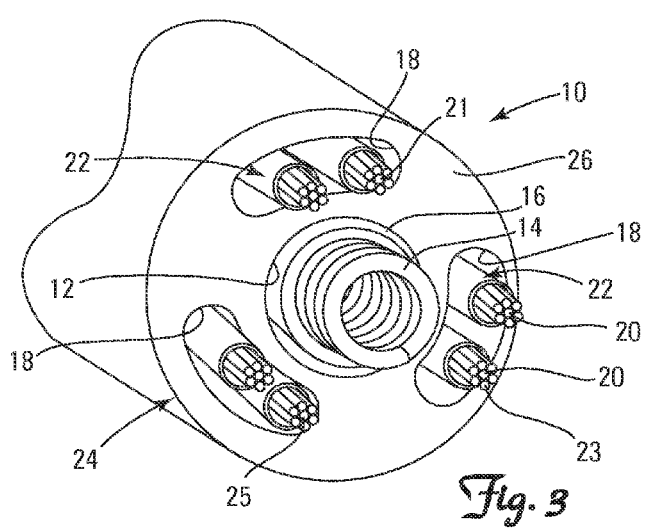
FIG. 3 is a cross-sectional view of the St. Jude Medical Riata® Lead, a multi-lumen ICD implantable cardiac lead.

FIGS. 2A, 2B and 3 depict known multi-lumen ICD defibrillation electrodes or leads that have been diagnosed with lead conductor anomalies. While these are indicative of the type of leads that can be diagnosed, anomalies in any type of defibrillation electrodes or leads are capable of being diagnosed with the methods and apparatus as disclosed herein. FIG. 2A depicts the Medtronic Quattro Secure® Lead. FIG. 2B depicts the Medtronic Sprint Fidelis® Lead. FIG. 3 depicts the St. Jude Medical Riata® Lead. The leads 10, while having various constructions, have similar features. These similar features are identified with the same reference numbers in the figures.

The implantable cardiac lead 10 is comprised of a lumen 12 and center inner pacing coil 14 surrounded by PTFE insulation 16, a plurality of lumens 18 each containing at least one conductor 20 with each conductor 20 surrounded by ETFE insulation 22, an outer insulating layer 24, and a silicone insulation 26 disposed between the lumen 12 and the outer insulating layer 24. The conductors 20 include a sense conductor 21, a high voltage RV conductor 23, and a high voltage SVC conductor 25. The lumens 18 are disposed in the silicone insulation 26. The conductors 20 carry electric current to the pace-sense electrodes 66, 68 high voltage RV coil 64 and high voltage SVC coil 62 (see FIG. 5).

Figure 4:
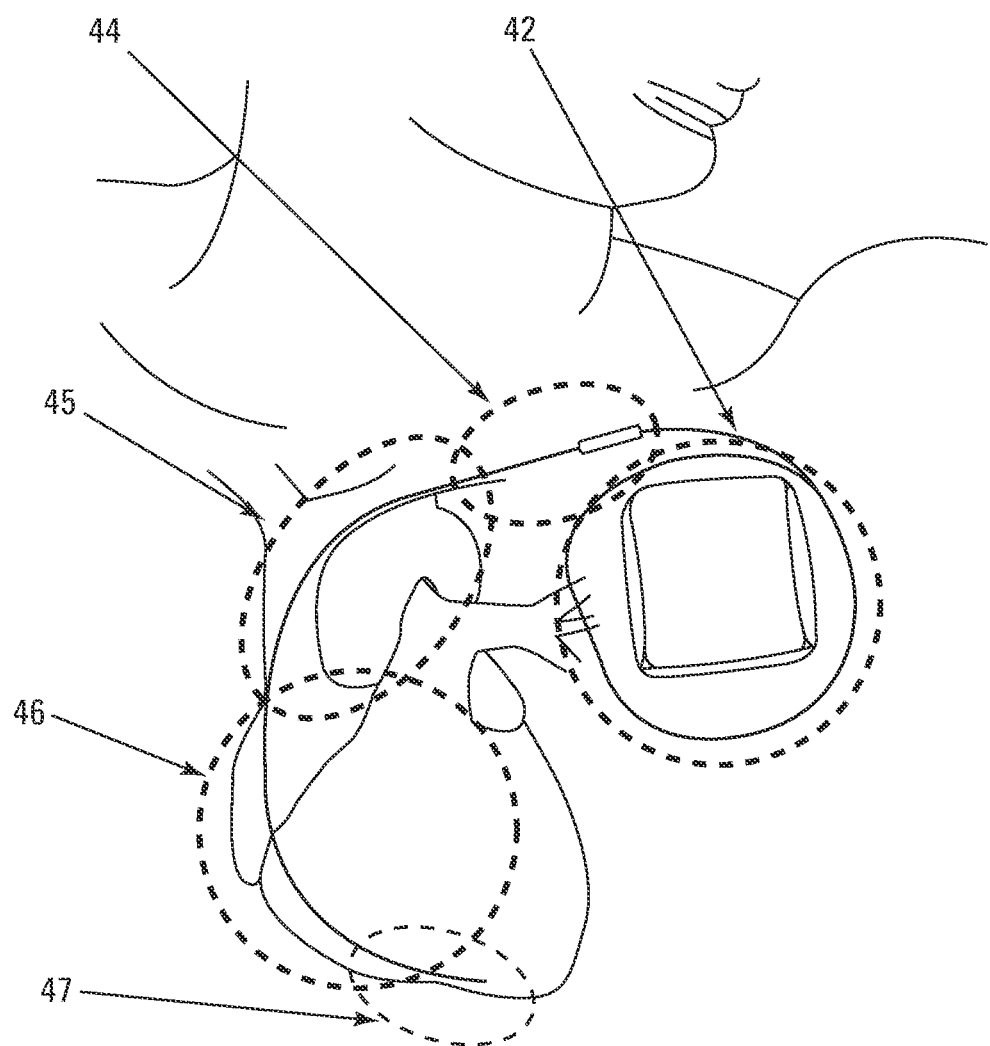
FIG. 4 illustrates regions within the human body associated with the implantation of an ICD and associated leads.

As shown in FIG. 4, lead failures most commonly occur at three regions along the course of a pacemaker or ICD lead 10. The first region 42 is proximate the pocket, caused either by abrasion of the lead 10 insulation 24 by pressure from the housing ("CAN") of the pulse generator or twisting of the lead 10 within the pocket. The second region 44 is that between the clavicle and first rib, where the lead 10 is subject to "clavicular crush." The third region 46 is the intracardiac region near the tricuspid valve. This third region 46 is a particularly common site of insulation 24 failure for the St. Jude Riata® lead 10 which is subject to "inside-out" insulation failure due to motion of the internal conductors 20 relative to the outer insulation 24.

Figure 5:
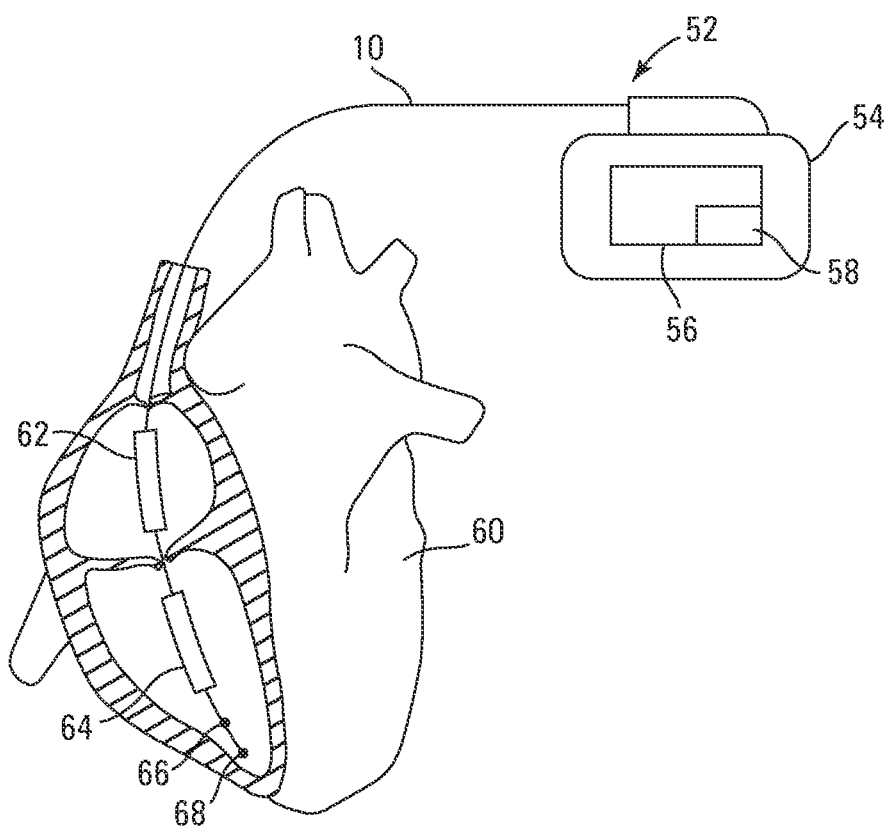
FIG. 5 shows an implantable medical device in which an embodiment of the present invention may be practiced. It shows an ICD pulse generator connected to a patient's heart via a transvenous cardiac lead used for pacing and defibrillation.

FIG. 5 depicts on ICD 52 implanted in the chest of a patient. The ICD 52 has an outer housing 54, commonly referred to as a "CAN," inner circuitry 56 and a battery 58. Connection is made to the heart 60 via the lead 10. The lead 10 can have an optional proximal defibrillation coil 62 which is near the superior vena cava (SVC) and is commonly referred to as the SVC coil 62. The lead 10 also has a distal defibrillation coil 64 which is commonly referred to as the right-ventricular coil or RV coil 64. Also shown is the optional "ring" pacing-sensing electrode 66. Located at the distal end of the lead 10 is the "tip" pacing-sensing electrode 68.

Figure 6:
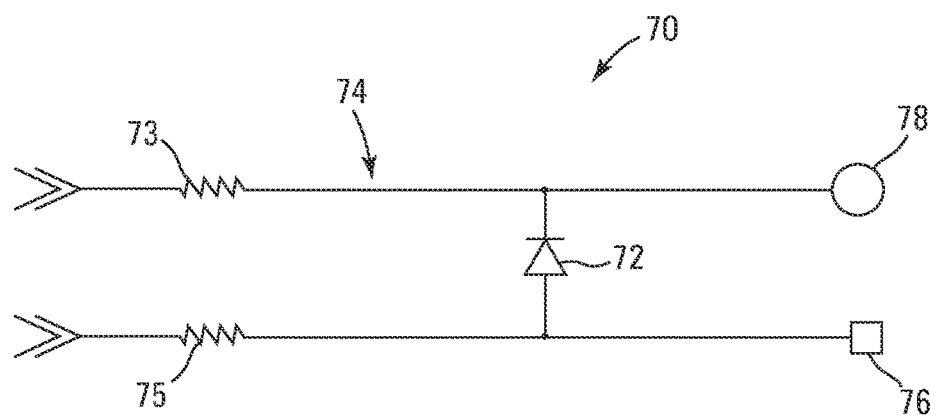
FIG. 6 shows a partial schematic of a pacemaker or ICD lead with the diode embodiment of the invention.

FIG. 6 depicts an embodiment of a circuit 70 in accordance with one aspect of the invention using a diode 72 as a small circuit element near the end of the lead to aid in identifying small changes in the lead impedance. Shown is a partial schematic of a pacemaker or ICD lead 74. The tip 76 and ring 78 of the lead 74 are used for both sensing and pacing. The sensed electrogram (EGM) signals are of low voltage (typically <30 mV) and thus the diode 72 will not conduct sensing current so it will not interfere with the sensing signals. Pacing is done with a negative voltage on the tip 76 (so-called "cathodal" pacing) and the diode 72 will be back-biased during this pacing pulse. Hence, the diode 72 will not interfere with pacing functions. Resistor 73 (shown as 13Ω) and resistor 75 (shown as 35Ω) are not discrete resistors but rather represent the resistances of the ring and tip conductors respectively.

Figure 7:
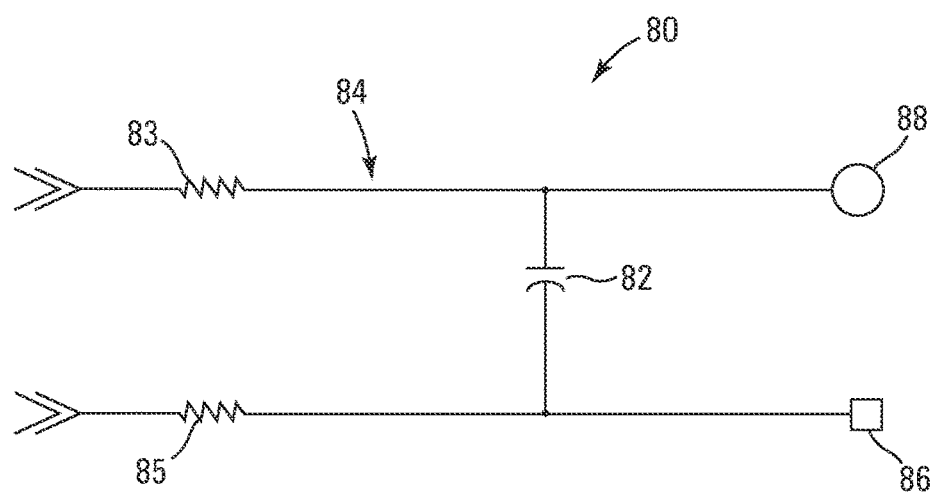
FIG. 7 shows a partial schematic of a pacemaker or ICD lead with the capacitor embodiment of the invention.

To determine an accurate conductor resistance measurement, a short positive pulse (e.g. 5 V) is fed to the tip 76 with respect to the ring 78 while the current is being monitored. The diode 72 will conduct this pulse and the conductor resistance can be accurately determined by Ohm's law. In the embodiment shown, resistor 73 can be 13Ω and resistor 75 can be 35Ω, but resistor 73, 75 are not so limited. The voltage used for the calculation will be the test voltage less the diode "drop" to allow for the voltage loss in the diode, e.g., 4.3 V=5 V—0.7 V. For example, in the situation where one of the two cables in the ring connection is broken then the total resistance will be increased from 48Ω to 61Ω. FIG. 7 depicts an embodiment of a circuit 80 in accordance with another aspect of the invention using a capacitor 82 as a small circuit element near the end of the lead to aid in identifying small changes in the lead impedance. Shown is a partial schematic of a pacemaker or ICD lead 84. Useful values for the capacitor 82 are 100 pF to 100 nF. The tip 86 and ring 88 of such a lead 84 are used for both sensing and pacing. The sensed electrogram (EGM) signals are of low frequency (typically <100 Hz) and the source impedance is about 1 KΩ. The time constant for the resulting low-pass filter is thus ranging from 100 ns to 100 μs and thus the capacitor 82 will not attenuate the sensing signals.

The pacing pulse is typically about 500 μs and the relevant resistance is that of the conductors which is about 48Ω total, where the value of the first resistor 83 is about 13Ω and the value of the second resistor 85 is about 35Ω. However, the values of the resistors 83, 85 are not so limited. Thus, the low-pass time constant seen by the pacing pulse is <5 μs and as such is immaterial to the pacing pulse.

To determine an accurate conductor resistance measurement, a moderate frequency signal is fed to the tip 86 with respect to the ring 88 while the current is being monitored. With a 100 nF capacitor 82 a 160 KHz signal is used. The capacitor impedance is then:

$$Z_c = 1/(2\pi f C) = 10\Omega.$$

Thus, changes of connection resistance of, for example, 13Ω, are easily detected. The approximate propagation speed V in an implantable cardiac lead, without anomalies, was determined using the following equation:

$$V = c/\sqrt{\kappa}$$

where c is the speed of light in a vacuum (30 cm/ns) and κ is the relative permeability of the insulator compared to a vacuum. The relative permeability is about 3 for silicone and about 2.5 for ETFE. For silicone insulation this results in an approximate propagation velocity of 17.3 cm/ns. This is approximate because the ICD implantable cardiac lead is more complex than a classic coaxial cable having a central conductor.

For an ICD implantable cardiac lead having a common length of 65 cm, the "round-trip" travel distance for wave propagation is 130 cm. The frequency is determined by:

$$f = V/\lambda$$

where λ is the wavelength of the test frequency. Thus, with a propagation velocity of 17.3 cm/ns, a frequency of about 66 MHz of corresponds to a ¼ wavelength over the implantable cardiac lead. At this frequency, transmission line effects dominate and a short (at the tip) appears to be an open circuit at the source. Hence, test frequencies must be much lower than this or transmission line corrections must be made. It is noted that for a 160 KHz test signal the wavelength is very long compared to the lead so this does not present an issue.

Alternatively, a smaller 10 nF capacitor 82 could be used with a test frequency of 1.6 MHz without problems. A 1 nF capacitor 82 could also be used with 16 MHz without resorting to transmission line corrections. A 100 pF capacitor 82 would require a test frequency on the order of 100 MHz and this can still be used albeit with transmission line corrections.

Figure 8:
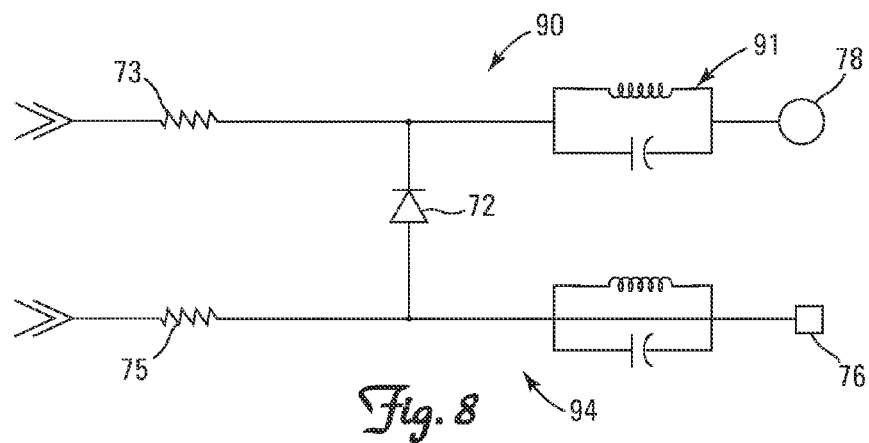
FIG. 8 shows a partial schematic of a pacemaker or ICD lead with the diode embodiment of the invention along with typical MRI protection components.

FIG. 8 depicts an embodiment of a circuit 90 in accordance with another aspect of the invention using the diode embodiment 70 in conjunction with typical MRI protection components as a small circuit element near the end of the lead 94 to aid in identifying small changes in the lead impedance. In another embodiment, the capacitor embodiment 80 can be used in conjunction with typical MRI protection components near the end of the lead 94. Shown is a partial schematic of a pacemaker or ICD lead 94. A well-known approach to limiting the conduction of the MRI RF signal is to insert an LC "tank" circuit 91 between the lead conductor and the electrode. Since this is distal to the impedance test component—a capacitor (as in FIG. 7) or diode 72—it will not affect the conductor impedance measurement.

Figure 9:
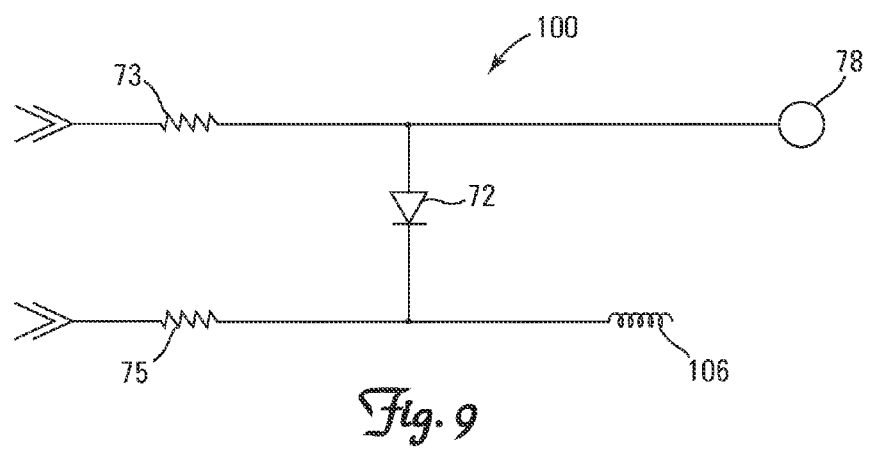
FIG. 9 shows a partial schematic of an ICD lead with the diode embodiment of the invention.

FIG. 9 depicts an embodiment of an ICD lead 100 using the diode embodiment 70 to aid in identifying small changes in the lead impedance. Shown is a partial schematic of an ICD lead 100. Conductor impedance measurements are performed as described earlier. The main phase pulse (up to 900 V) of a defibrillation shock is preferable positive (on the RV coil 106 with respect to the body) and thus the diode 72 will not conduct. For the negative ($2^{nd}$ phase), the diode 72 will conduct and pass some current thru the diode 72 and the ring 78 electrode. This is expected to be acceptable as some popular ICD leads (so-called "integrated bipolar" type) dispense with the ring electrode altogether and thus deliver current to the ring anatomical position—near the tip— without causing significant performance problems.

The embodiment of FIG. 9 has two advantages over the "integrated bipolar" lead. The first is that less than one-quarter of the energy is shared with the ring as the diode blocks the much stronger positive phase. The peak current (important for electroporation stunning) is also cut in half or more. Second, after the defibrillation shock is delivered, the ring is quickly available for normal "true bipolar" sensing.

In another embodiment, a capacitor embodiment 80 could be used for the RV coil conductor impedance measurement. The capacitance ranges discussed earlier are acceptable and would not conduct sufficient energy or current to cause damage. While there would be a short high-current spike, its duration would be too short to cause electroporation stunning.

In general, the input impedance $Z_{in}$ of a transmission line, with an excitation wavelength of, is given by:

$$Z_{in} = Z_0 \frac{Z_L + jZ_0 \tan(\beta l)}{Z_0 + jZ_L \tan(\beta l)}$$

where $=2\pi/Z_L$ is the load impedance, and $Z_0$ is the characteristic impedance of the transmission line.

For the special case where a frequency with a multiple of a half-wavelength (of the lead) is used, the tangent terms become 0 and the equation reduces to:

$$Z_{in} = Z_L$$

so that the input impedance equals the load impedance.

Modern ICD leads are complex and hence their impedance spectra are more complex than the ideal simple transmission line.

Figure 10:
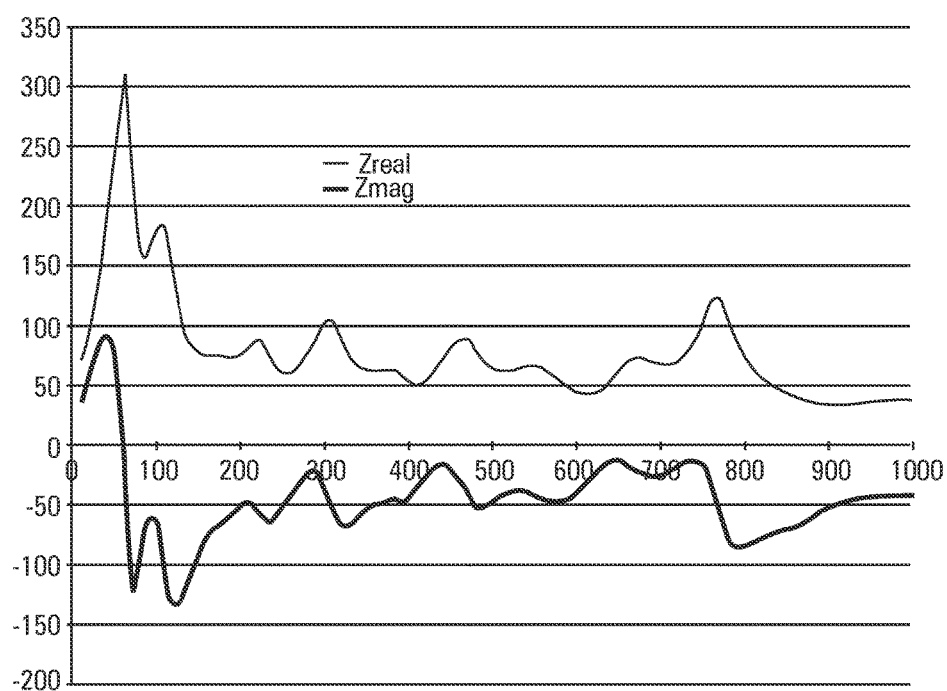
FIG. 10 depicts a plot of the impedance spectra of a Ring cable.

The plot of the impedance spectra of a Ring cable is shown in FIG. 10. It will be seen that the real impedance climbs towards a peak near the ¼ wavelength frequency of about 67 MHz. The real impedance then decreases and fluctuates between 50Ω and 100Ω. The imaginary part goes negative at about the same point and has a negative peak at about ½ wavelength (about 133 MHz). It then fluctuates between 20Ω and 60Ω.

Thus, for a practical system, the impedance spectra would be determined for the ICD lead (in physiologic saline) both with and without a broken cable. In actual clinical use, the spectra best matching the findings would indicate whether a cable was broken or not.

Figure 11:
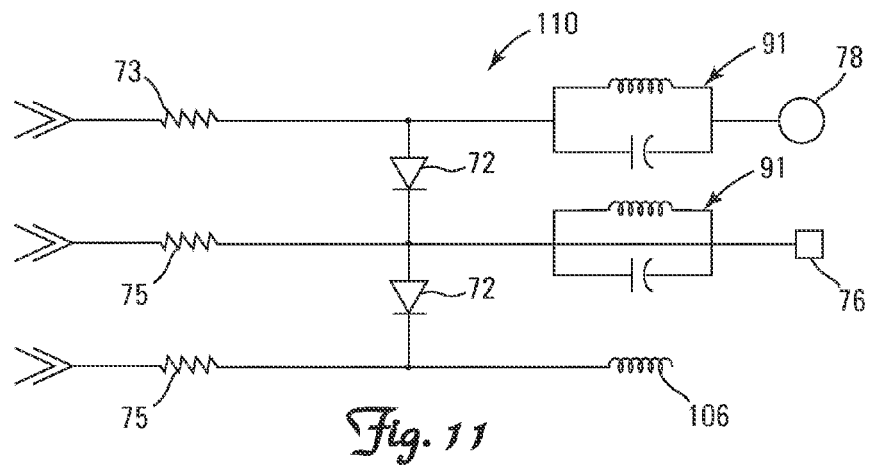
FIG. 11 shows a partial schematic of an ICD lead with the diode embodiment of the invention along with typical MRI protection components.

FIG. 11 depicts an embodiment of an ICD lead 110 using the diode embodiment 70 along with typical MRI protection components 91 to aid in identifying small changes in the lead impedance. Shown is a partial schematic of an ICD lead 110. This embodiment depicts the combination of the impedance-testing diode 72 for both the tip-ring conductor pair and the RV coil-ring conductor pair. Because of the diode 72 configuration, this approach has the disadvantage of conducting some of the negative ($2^{nd}$) phase current thru the tip. However, the MRI LC tank 91 would be expected to limit this current to a low value.

Figure 12:
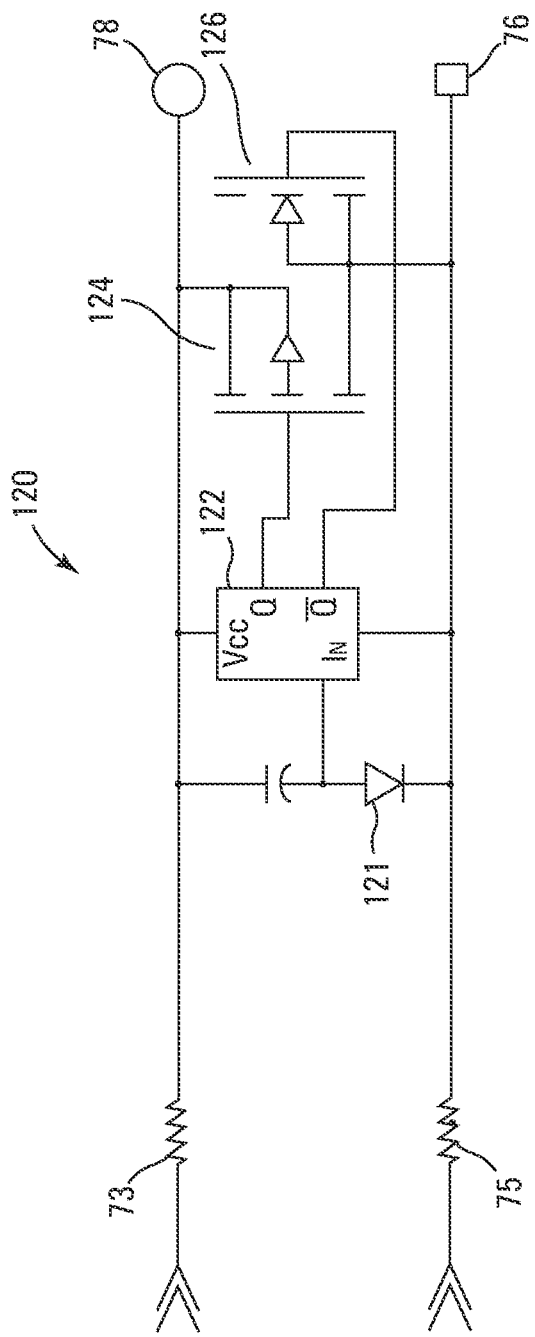
FIG. 12 shows a partial schematic of an ICD lead with a solid state embodiment of the invention.

FIG. 12 depicts a solid state implementation 120 of an embodiment of the invention. The diode 121 and capacitor 123 scavenge a small amount of charge from the pacing pulses. If testing is required and there have been no pacing pulses, then a few are delivered to charge up the distal capacitor which then powers the digital circuit shown in the block diagram of FIG. 12.

For lead testing, special sequence of pulses can be delivered to the pacing tip which would not have any pacing effect. For example, ten pulses each of 10 μs in duration. This pulse sequence is recognized by the digital block 122 which then gives complementary drives to the two enhancement mode MOSFETs 124, 126 shown. In parallel they function as a resistor and provide a low impedance path between the tip 78 and the ring 76 for a short period of time to allow an accurate impedance measurement.

In one embodiment, the short period of time is typically <1 second so as to not interfere with pacing and sensing. This time duration is determined by a small capacitor connected to the digital circuit (not shown) or alternatively by using an integrated capacitor within the digital circuit.

It will be understood that other variations of a small circuit element in accordance with the various embodiments of the present invention may be used to accomplish a similar function. While the small circuit element may be a single passive circuit element, or a small combination of active circuit elements, these embodiments of the small circuit element feature a limited circuit functionality that may be easily incorporated into the distal end of a lead without the overhead, expense, size or power consumption of a larger control circuit or microcontroller. Alternatively, elements of different ones of the various embodiments of the small circuit element may be combined.

The values noted above are example embodiments and should not be read as limiting the scope of this invention. Those skilled in the art will recognize that the above values may be adjusted to practice the invention as necessary depending on the electrode implantable cardiac lead technology used and the physical characteristics of the patient.

While the present invention has been described with reference to certain embodiments, those skilled in the art should appreciate that they can readily use the disclosed conception and specific embodiments as a basis for designing or modifying other structures for carrying out the same purposes of the present invention without departing from the spirit and scope of the invention as defined by the appended claims.

The invention claimed is:

1. An implantable medical system comprising:
an implantable lead that includes a small circuit element positioned within a distal end of the lead and continuously electrically connected between a ring conductor of the lead and one of a tip conductor or a stimulation electrode; and
an implantable electromedical device to which the implantable lead is adapted to be connected, the device including a control system programmed to cause:
a therapeutic pulse to be selectively delivered to the stimulation electrode, and
a DC pulse to be periodically delivered to the lead through the small circuit element to test for a partial conductor failure by automatically calculating a resistance for the DC pulse through the small circuit element and providing an indication of a partial conductor failure based upon the resistance for the DC pulse through the small circuit element;
wherein the small circuit element remains electrically connected between the ring conductor of the lead and one of the tip conductor or the stimulation electrode when the therapeutic pulse is being delivered.

2. The system of claim 1 where the device causes the DC pulse to be delivered as a moderate frequency signal to the lead.

3. The system of claim 1 wherein the small circuit element is a passive circuit selected from the set consisting of a diode, a capacitor, a diode, and a LC tank circuit.

4. The system of claim 1 wherein the small circuit element is an active circuit including a diode and capacitor circuit controlled by a digital circuit, and wherein device causes a trigger signal to be delivered to the lead to activate the active circuit element for a short period of time during which the DC pulse is caused to be delivered.

5. The system of claim 1 wherein the small circuit element is positioned in the distalmost 10 cm of the lead.

6. The system of claim 1 wherein the small circuit element is a capacitor between the ring conductor and the tip conductor.

7. The system of claim 1 wherein the small circuit element is a capacitor is between the ring conductor and the stimulation electrode conductor.

8. The system of claim 1 wherein the small circuit element is a diode between the ring conductor and the tip conductor.

9. The system of claim 1 wherein the small circuit element is a diode between the ring conductor and the electrode conductor.

10. A medical system comprising:
an implantable lead that is adapted to be implanted in a patient and includes a small circuit element positioned within a distal end of the lead and continuously electrically connected between a ring conductor of the lead and one of a tip conductor or a stimulation electrode; and
an external test device to which the implantable lead is adapted to be connected, the test device including a control system programmed to cause:
a therapeutic pulse to be selectively delivered to the stimulation electrode, and
a DC pulse to be periodically delivered to the lead through the small circuit element to test for a partial conductor failure of the lead by automatically calculating a resistance for the DC pulse through the small circuit element and providing an indication of a partial conductor failure based upon the resistance for the DC pulse through the small circuit element;
wherein the small circuit element remains electrically connected between the ring conductor of the lead and one of the tip conductor or the stimulation electrode when the therapeutic pulse is being delivered.

11. The system of claim 10 where the device causes the DC pulse to be delivered as a moderate frequency signal to the lead.

12. The system of claim 10 wherein the small circuit element is a passive circuit selected from the set consisting of a diode, a capacitor, a diode, and a LC tank circuit.

13. The system of claim 10 wherein the small circuit element is an active circuit including a diode and capacitor circuit controlled by a digital circuit, and wherein device causes a trigger signal to be delivered to the lead to activate the active circuit element for a short period of time during which the DC pulse is caused to be delivered.

* * * * *